United States Patent [19]
Joseph et al.

[11] Patent Number: 5,419,322
[45] Date of Patent: May 30, 1995

[54] INTERNAL APPARATUS FOR CONTINUOUS ELECTRICAL AND OXIMETRIC INTRAPARTUM MONITORING OF THE FETUS

[76] Inventors: Barry M. Joseph; Francine A. Guzman, both of One Round Hill Rd., Lake Success, N.Y. 11020

[21] Appl. No.: 96,563

[22] Filed: Jul. 22, 1993

[51] Int. Cl.⁶ .......................................... A01B 5/0448
[52] U.S. Cl. ...................... 128/634; 128/642
[58] Field of Search ............... 128/632, 633, 634, 635, 128/636, 666, 642

[56] References Cited

U.S. PATENT DOCUMENTS

| | | |
|---|---|---|
| Re. 28,990 | 10/1976 | Hon . |
| 4,149,528 | 4/1979 | Murphy . |
| 4,220,110 | 9/1980 | Peterson et al. . |
| 4,320,764 | 3/1982 | Hon . |
| 4,394,572 | 7/1989 | Wilber . |
| 4,437,467 | 3/1984 | Helfer et al. . |
| 4,501,276 | 2/1985 | Lombardi . |
| 4,658,825 | 8/1987 | Hochberg et al. . |
| 4,968,173 | 11/1990 | Yount . |
| 5,046,965 | 9/1991 | Neese et al. . |
| 5,109,849 | 5/1992 | Goodman et al. ................ 128/633 |
| 5,127,407 | 7/1992 | Tan . |
| 5,154,175 | 10/1992 | Gunther ............................ 128/633 |
| 5,193,542 | 3/1993 | Missanelli et al. . |

FOREIGN PATENT DOCUMENTS

| 0009016 | 10/1989 | WIPO ............................ 128/633 |
|---|---|---|
| 9118549 | 12/1991 | WIPO ............................ 128/634 |

OTHER PUBLICATIONS

Severinghaus et al., "Recent Developments in Pulse Oximetry," *Anesthesiology*, vol. 76, pp. 1018-1038, 1992.
Garosi et al., "Adaptation of Pulse Oximetry for Fetal Monitoring During Labor," *The Lancet*, vol. 337, pp. 1265-1267, May 25, 1991.
Hay et al., "Pulse Oximetry in Neonatal Medicine," *Clinics in Perinatology*, vol. 18, No. 3, pp. 441-472, Sep. 1991.
Bowes, "Pulse Oximetry: A Review of the Theory, Accuracy and Clinical Applications," *Obstetrics Gynecology*, vol. 74, pp. 541-546, 1989.

*Primary Examiner*—Lee S. Cohen
*Assistant Examiner*—Brian M. Green
*Attorney, Agent, or Firm*—Collard & Roe

[57] ABSTRACT

An internal apparatus for continuous electrical and oximetric intrapartum fetal monitoring includes a base assembly containing a photodetector and a single spiral probe extending from the base assembly, which probe penetrates a fetal scalp. The probe contains an optical fiber having a light source which directs an emerging cone of light toward said photodetector. The probe also contains means for connecting the photodetector to an external monitor and means for connecting the spiral probe to the external monitor, whereby the internal apparatus measures the arterial hemoglobin oxygen saturation of the fetus.

16 Claims, 3 Drawing Sheets

FIG. 5
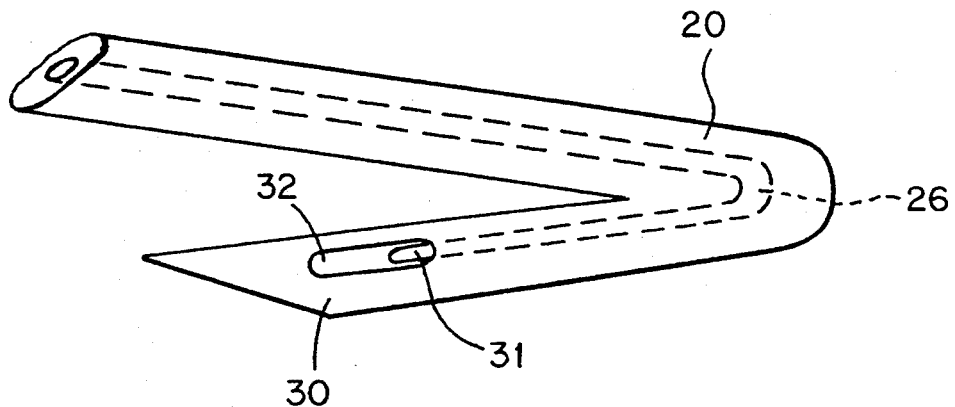
FIG. 6
FIG. 7
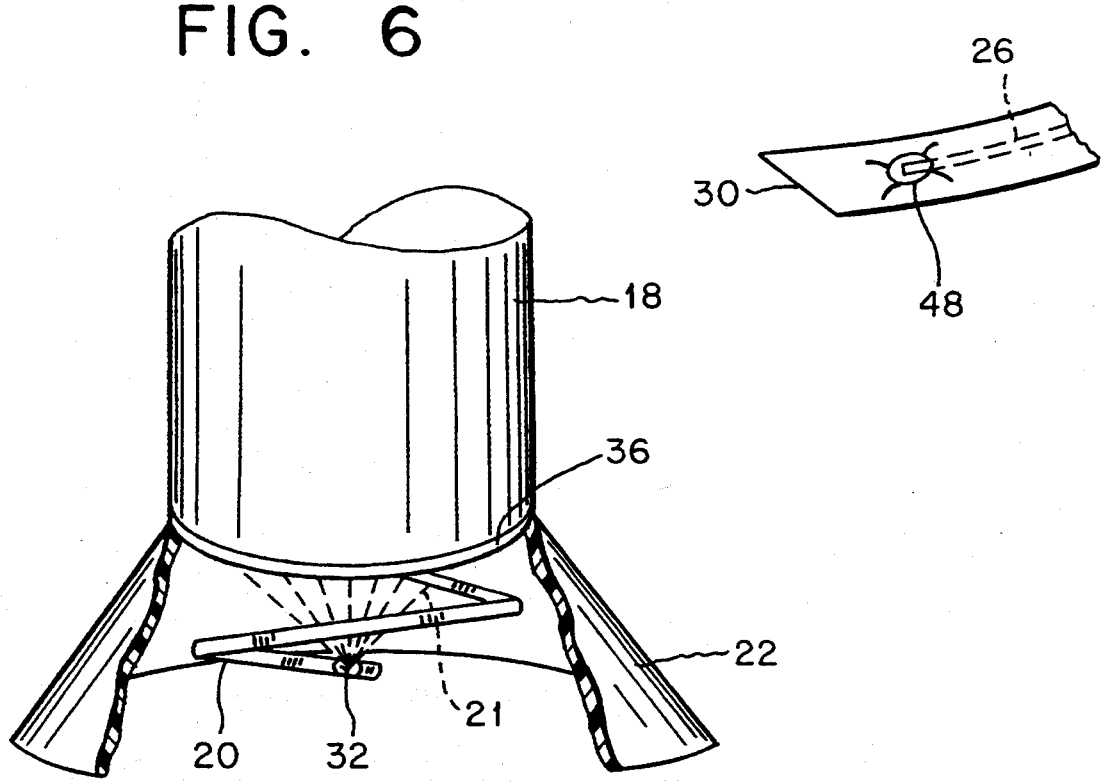

INTERNAL APPARATUS FOR CONTINUOUS ELECTRICAL AND OXIMETRIC INTRAPARTUM MONITORING OF THE FETUS

BACKGROUND OF THE INVENTION

1. Field of the Invention

The present invention relates to the application of pulse oximetric principles to continuous fetal monitoring and, more particularly, to an oximetric apparatus, inserted subcutaneously into the fetus, capable of measuring the oxygen saturation of arterial hemoglobin as well as fetal heart rate (FHR) and electro-cardiogram (EKG) activity during the labor process.

2. The Prior Art

The concept of fetal monitoring during the labor process is well-known and established in the field of obstetrics. The introduction of various electrode devices which attach to the fetal scalp and record FHR and EKG activity of the fetus provided the initial basis for monitoring. (See U.S. Pat. No. Re 28,990 issued to Hon Oct. 1976.) It soon became evident that FHR and EKG activity did not by itself adequately or accurately reflect fetal well-being during labor.

Subsequently, a technique for evaluating fetal well-being by lacerating the fetal scalp, collecting a blood sample and analyzing this sample for a Ph measurement was developed. It should be noted that pH measurements on interstitial fluid of the scalp were often erroneous when compared to pH measurements on blood samples collected from the scalp.

Measuring the pH value of the fetus was an important assessment of fetal well-being because the pH value reflected the arterial oxygenation of the fetus, the importance of which is self-evident. Although scalp pH measurements are an indispensable tool in fetal assessment, these measurements are taken on an intermittent basis and are an invasive and cumbersome procedure.

Various attempts to develop continuous pH monitoring devices have been either clinically impractical or not feasible. One attempt was a spiral-type device shown in the U.S. Pat. No. 4,320,764. Another pH probe was disclosed in the Peterson et al. U.S. Pat. No. 4,220,110, and was modified for continuous pH monitoring in the Hockberg et al. U.S. Pat. No. 4,658,825. The spiral probe is attached to the epidermis of the fetus. This probe consisted of an ion-permeable membrane envelope which is enclosed at the ends by a pair of optical fibers. The probe, which contains pH-sensitive dye, changes color in response to the hydrogen ion concentration of the interstitial fluid of the fetal scalp. This color change is optically detected and quantified. In addition, the spiral probe also functions to provide FHR and EKG activity by virtue of its contact with the fetal scalp. It should be noted that fetal pH measurements on interstitial fluid have often been erroneous when compared to blood samples, largely due to the common occurrence of caput or swelling of the fetal head during the labor process. In addition, it should be noted that while this probe may provide FHR and EKG activity and pH measurements (albeit often erroneous values), it cannot, by its design, measure the oxygen saturation of arterial hemoglobin. Other design deficits include an unacceptable and non-sterile method of application and a spiral probe which is twice the diameter of conventional probes, and penetrates to five times the depth in the fetal scalp. This size differential would inevitable increase the trauma to the fetus. Accordingly, because of the considerations cited above, this apparatus has not been successfully commercialized.

The principle of pulse oximetry is based upon positioning a pulsating arterial bed between a light source and a photodetector, as shown in the Wilber U.S. Pat. No. 4,394,572. The light source emits wavelengths of red and infrared light which correspond to absorption peaks of oxyhemoglobin (oxygen saturated hemoglobin) and deoxyhemoglobin (unsaturated hemoglobin) in red blood cells entering the arterial capillaries during systole. A background absorption occurs from the hemoglobin remaining in small vessels during diasystole. By utilizing the pulsatile nature of arterial blood, the oximeter is able to separate out the absorption measurements eliminating the measurements of static or non-pulsatile components, namely, venous blood and other tissue components. By rapidly alternating the wavelengths of light transmitted through the tissue, the difference in absorption for total hemoglobin and oxyhemoglobin can be measured for each pulse of arterial capillary blood. An estimated percentage of oxygenated hemoglobin in each pulse can then be calculated from the difference in absorption.

In this way, a precise beat-to-beat calculation of arterial hemoglobin oxygen saturation (AHOS) can be obtained without interference from surrounding venous blood or other tissue components.

The concept of applying the principles embodied within pulse oximetry to fetal monitoring have long posed a number of well-known difficulties, including the inaccessibility of the fetal head and fetal parts, the clinical necessity for monitoring the fetus during early labor with minimal cervical dilation, and attaining sufficient stability in its application to avoid dislodging during labor.

Other prior art attempts to solve these past difficulties are as follows.

The Missanelli et al. U.S. Pat. No. 5,193,542 attempts to perform oximetric fetal monitoring using an apparatus in a T-shaped configuration which consists of a pair of interfacing jaws that clamp onto fetal scalp tissue. The upper jaw houses a pair of LEDs (light source) and the lower jaw houses a pair of photodetectors.

This prior art apparatus has not been used successfully in a clinical setting to date, as evidenced by the fact that there are no published reports of its use available. This device will be difficult at best to apply to the smooth oval-shaped fetal head. Moreover, the constant twisting and moving which occurs by mother and fetus during labor will result in frequent slipping and dislodging of the device. To compound the problems of application and stability, the fetal head (the vertex presentation overwhelmingly predominates in obstetrics at 96%) is often covered in fetal hair and vernix, a white, oily cheese-like material which covers the fetus in utero, as well as other bodily fluids such as blood (maternal), amniotic fluid, fetal meconium, etc. These materials will not only hamper the application, but may result in inaccurate measurements. It should also be noted that this device does not provide for EKG activity. In addition, although precise dimensions are not given by Missanelli, it is difficult to believe that this device, if applied, could be done so before active labor is established.

The Lombardi U.S. Pat. No. 4,501,276 discloses a fetal electrode apparatus. The apparatus consists of an insertion device, such as a hollow tube with a semi-rigid form, and a fetal electrode assembly. The electrode assembly has a piston member such that the electrodes within the insertion device may be pushed out to pierce the fetal head when the insertion device comes in contact with the fetus. The electrodes are designed with beveled edges for piercing the fetal head without having to drill a hole separately. Furthermore, the electrodes do not incorporate using light means for monitoring the fetus.

The Murphy U.S. Pat. No. 4,149,528 discloses an electrode assembly for sensing heart activity, which consists of a guide tube assembly (again a hollow plastic-like tube) with a spiral retaining coil electrode disposed at one end and a handle at the other. By rotating the handle, the spiral retaining coil, which moves on a threaded track, emerges from the opposite end of the guide tube and engages the fetal scalp. A second electrode for monitoring is also disposed at the end of the guide tube and engages the fetal scalp. A second electrode for monitoring is also disposed at the end of the guide assembly in the holder of the spiral retaining coil. The two electrodes are connected to signal leads which are externally connected to the monitoring device. After connection with the fetal scalp, the guide assembly detaches from the electrode holder and the signal leads, thereby leaving just the lead wires and electrodes in place. The invention does not show the use of LEDs or other light measurement means for the electrodes.

The Helfer et al U.S. Pat. No. 4,437,467 discloses an apparatus for monitoring fetal heartbeat and the like, and this apparatus is very similar to that of the Murphy patent, in that there is an elongated guide tube which has an electrode coil assembly at one end for engaging the fetal scalp. The opposite end of the guide assembly has a handle that rotates the electrode coil assembly such that the coiled electrode assembly will pierce the fetal scalp. Furthermore, the use of light means for the electrodes is not disclosed.

The Tan U.S. Pat. No. 5,127,407, discloses an epidural oxygen sensor. In one embodiment, the sensor is comprised of a thin rubber-like probe that is inserted into the skull of the fetus. The sensor utilizes LEDs and a photo detector to monitor the oxygen saturation of blood within the skull of the fetus. The sensor is inserted through a burr hole drilled in the skull separately. In another embodiment, the LEDs and photo detector are situated within a hollow bone screw. The sensor in this embodiment is then screwed into the skull of the fetus at the desired depth. Upon receiving light sensors from the LEDs, the photo detector converts these signals to electrical signals for processing by external equipment.

The Hochberg et al U.S. Pat. No. 4,658,825 discloses a spiral probe for simultaneous electrical and chemical monitoring of a fetus, which includes a spiral-shaped needle which serves as an EKG electrode, and also houses a fiber optic pH probe. This combined probe is made of a soft material such as silicon plastic. An elongated guide tube is used to secure the probe in place and is then removed once it is secured to fetus. The fiber optic pH probe utilizes a separate light source and light sensor for monitoring the fetal pH. The light sensor here serves the same function as the photo detectors explained above. The needle electrode for EKG monitoring is also connected to an external monitoring device.

The Yount U.S. Pat. No. 4,968,137, and Neese et al. U.S. Pat. No. 5,046,965, relate generally to fetal monitoring.

Other literature articles of interest include the following:
1. John W. Severinghaus, M.D. et al., "Recent Developments in Pulse Oximetry," *Anesthesiology*, Vol. 76, pp. 1018-1038, 1992.
2. Jason O. Gardosi et al., "Adaptation of Pulse Oximetry for Fetal Monitoring During Labor," *The Lancet*, Vol. 337, pp. 1265-1267, May 25, 1991.
3. William W. Hay, Jr., M.D. et al., "Pulse Oximetry in Neonatal Medicine," *Clinics in Perinatology*, Vol. 18, No. 3, pp. 441-472, September 1991.
4. Watson A. Bowes III, M.D. et al., "Pulse Oximetry: A Review of the Theory, Accuracy and Clinical Applications," *Obstetrics Gynecology*, Vol 74, pp 541-546, 1989.

However, the most troublesome aspect of all this prior art apparatus is the risk of trauma to the fetus. Clamping a fold of tissue for extended periods of time with sufficient pressure to maintain stability of the probe would likely result in necrosis of the clamped skin fold, not to mention the risk of burns from the heat generated from the light sources over long periods of time on particularly vulnerable fetal skin surfaces.

Therefore, it is desirable to be able to provide an oximetric apparatus which is convenient to use and practical to apply to the fetal head during early as well as active phases of labor. The apparatus must minimize trauma to the fetus and provide continuous measurements, including the arterial oxygenation levels in the fetus, as well as conventional FHR and EKG activity. Heretofore, although many devices for fetal monitoring have been proposed in the prior art, they have not been successful to date in overcoming the numerous problems recognized in the art, and have failed to provide the critical measurements which accurately reflect fetal well-being during labor.

SUMMARY OF THE INVENTION

It is an object of the present invention to provide a clinically practical oximetric fetal monitoring apparatus providing continuous assessment of arterial oxygenation measurements necessary for determining fetal well-being during labor, and being applied with a firm, stable contact to the fetal scalp, whereby trauma to the fetal head is minimized.

It is a further object of the present invention to provide an oximetric fetal monitoring apparatus which eliminates the risk of pressure necrosis and heat emission to fetal tissue and permits monitoring during early labor with minimal cervical dilation.

The clinical importance of the present invention will set new standards in accessing fetal well-being during labor. The amount of oxygen bound to hemoglobin in arterial blood represents the supply of available oxygen to critical body tissues such as the brain and heart. Thus, an insufficient or low supply of oxygen as manifested by decreasing AHOS values would identify a hypoxemic state (less than 70% saturation) in the fetus, and provide an early indication of a fetus in distress. In this way, timely medical intervention may be accomplished before a prolonged, severe hypoxemia (below 60% saturation) in the fetus results in permanent and irreversible brain damage.

The above objects are achieved in accordance with the present invention by providing a spiral probe capable of simultaneous and continuous electrical and oximetric monitoring of a fetus. The probe includes a solid base element with a modified rubber collar, from which extends a spiral-shaped helical probe which is inserted into the fetal scalp. Light is conveyed through the base and to the end of the spiral probe by an optical fiber. The light emerges through an opening directed toward the base element which houses the photodetector. In this way, the light emerges from the spiral probe, passes through the arterial vascular bed of subcutaneous scalp tissue, and is detected by the photodetector on the base element from which the spiral probe originated. The spiral probe is electrically conductive and thus, when in contact with fetal scalp tissue, provides FHR and EKG activity measurements.

BRIEF DESCRIPTION OF THE DRAWINGS

Other objects and features of the present invention will become apparent from the following detailed description considered in connection with the accompanying drawings which disclose embodiments of the present invention. It should be understood, however, that the drawings are designed for the purpose of illustration only and not as a definition of the limits of the invention.

In the drawings, wherein similar reference characters denote similar elements throughout the several views:

FIG. 5 is an enlarged view of the embodiment of the end of the spiral probe of FIG. 1;

FIG. 6 is an enlarged partially broken out view of the spiral probe of FIG. 2; and FIG. 7 is an enlarged partially broken out view of another embodiment of the spiral probe.

DETAILED DESCRIPTION OF PREFERRED EMBODIMENTS

Figure 1:
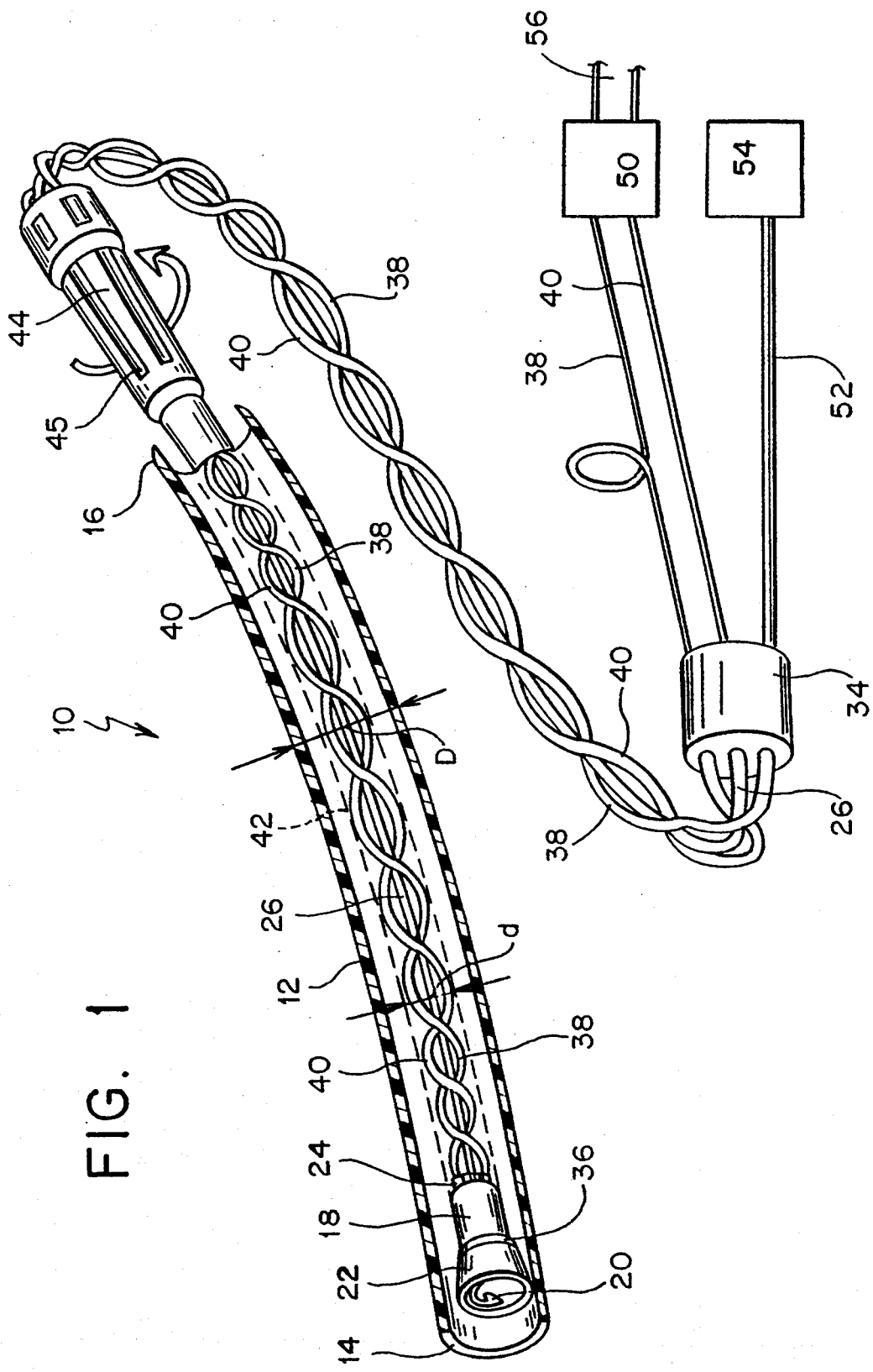
FIG. 1 is a perspective view of the electrical/oximetric spiral probe apparatus of one embodiment of the present invention.
Figure 2:
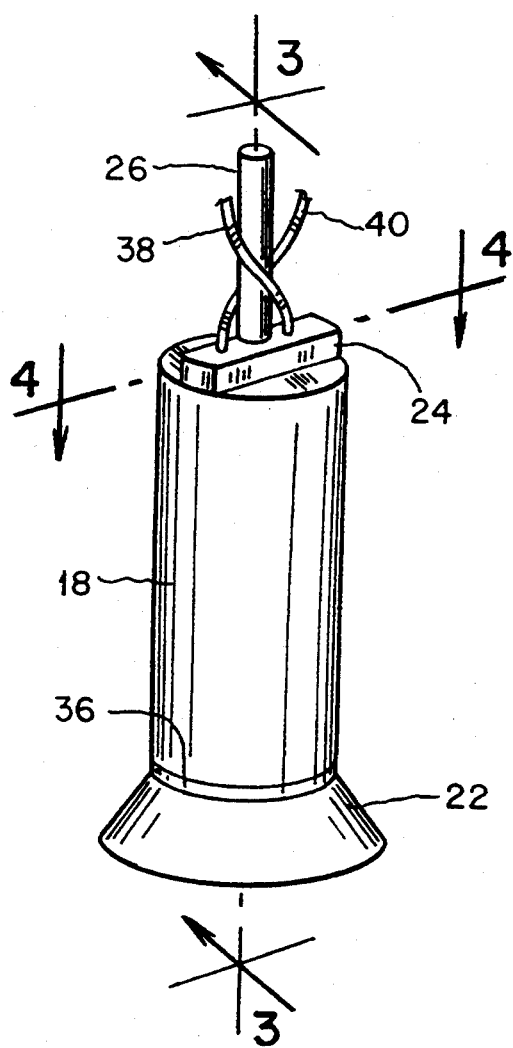
FIG. 2 is a front view of the spiral probe of FIG. 1.
Figure 3:
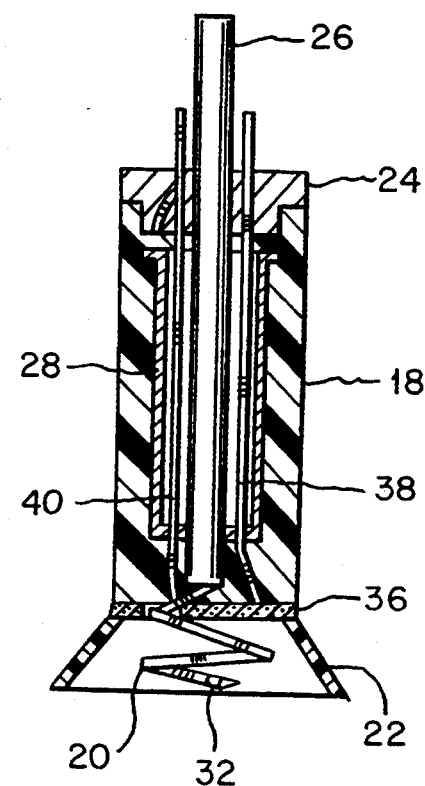
FIG. 3 is a cross-sectional view along line 3—3 of the probe of FIG. 2.
Figure 4:
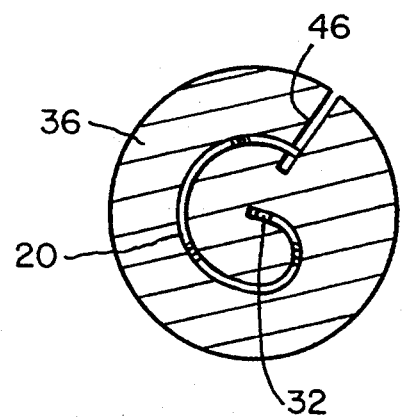
FIG. 4 is a cross-sectional view along line 4—4 of the probe of FIG. 2.

Turning now in detail to the drawings, FIG. 1 shows an embodiment of the electrical/oximetric fetal monitoring apparatus of the present invention. The apparatus 10 comprises a flexible hollow plastic outer tube 12 which serves as a guide tube whose proximal end 14 is positioned adjacent to the fetal head and the distal end 16 extends outside the mother's body. As shown in FIGS. 2–4, a plastic base assembly 18 is disposed in the proximal end 14. Molded into and extending from the plastic base assembly 18 is a metallic spiral-shaped helix probe 20. The plastic base is surrounded by a rubber collar 22 which contains an electrical reference electrode 24.

An optical fiber 26 passes centrally, as shown in FIG. 3, down through a metal cylinder 28 within the base assembly 18 into the spiral probe 20 terminating near the beveled point 30 of the helix. The terminal end 31 of the optical fiber 26 exits the spiral helix 20 through an opening 32 which is aligned and positioned in direct relation to the base assembly 18, as shown in FIG. 3. Terminal end 31 functions as the light source.

Thus, light flows down the optical fiber 26 from its external source 34, centrally through the base assembly 18, traverses the spiral 20, and exits through the light source 31 at opening 32 which directs the light 21 back toward the base assembly (FIG. 6), where the photodetector 36 is situated on the bottom of the base assembly (FIGS. 3 and 6). A first pair of electrical wires 38 connects the photodetector 36 to an amplifier and external monitor 50. In addition, a second pair of electrical wires 40 connects the spiral probe 20 and reference electrode 24 to the external monitor 50. Wires 38 and wires 40 are wrapped around each other and are wrapped around optical fiber 26. These wires and the optical fiber are contained within inner tube 42.

Referring to FIG. 1, disposed in the proximal end 14 of the guide tube 12 is the base assembly 18 described above, which is extendable to be attached to the fetal scalp. Within the guide tube is a smaller diameter, flexible, hollow, plastic inner tube 42 which encloses the optical cable and wires within the guide tube 12 with its proximal end notched around the reference electrode 24 of the base assembly. Hollow tube 42 has an external diameter d which is smaller than the internal diameter D of guide tube 12. At the distal end 16 is an integrally attached handle assembly 44. The handle has finger grip notches 45 to assist the user in applying the apparatus. The guide tube 12 is inserted and placed adjacent to a suitable bony surface on the fetal scalp. Extending externally to the mother, the handle 44 can be rotated, resulting in clockwise rotation of the base assembly 18 and insertion of the spiral probe 20 into the fetal scalp, preferably to a depth of approximately 1 to 2 mm.

As shown in FIG. 1, the light source 34 is located external to the mother, and the optical fiber 26 transmits the light to the fetal scalp. In this way, trauma to the fetus via heat emission and pressure necrosis from previously described prior art probes is eliminated.

As shown in FIGS. 2–4, the spiral probe 20 may provide measurements of arterial hemoglobin oxygen saturation and FHR by oximetric means. However, EKG activity requires direct electrical contact and is beneficial in cases of fetal arrhythmias. Therefore, this capability is integrated into the monitoring apparatus.

As shown in FIG. 4, the purpose of the notch 46 in photodetector 36, with the notch measuring approximate 0.5 cm in diameter, is to facilitate assembly of the base.

The optical fiber 26 shown in FIG. 5 terminates at an aperture 32 on the spiral probe 20 positioned at approximately 2 o'clock. The aperture 32 as shown in FIG. 6 may be altered to displace the emerging light 21 more advantageously. In addition, the end of the optical fiber 26 may be modified in a concave structure 48 to further widen the emerging cone of light, as shown in FIG. 7. In addition, FIG. 5 shows that the spiral end has bevel 30 to allow easy and secure penetration of the fetal scalp.

FIG. 1 shows that light source 34 is connected by cable 52 to power control means 54 which is connected to external power supply 56.

The embodiments disclosed herein provide for continuous electrical and oximetric monitoring and assessment of the fetus during the labor and delivery process. The oximetric apparatus is inserted internally beneath the skin of the fetus and allows for the direct measurement of arterial hemoglobin oxygen saturation. The apparatus is practical and clinically feasible to apply to the fetus.

While several embodiments of the present invention have been shown and described, it is to be understood that many changes and modifications may be made thereunto without departing from the spirit and scope of the invention as defined in the appended claims.

What is claimed is:

1. An internal apparatus for continuous electrical and oximetric intrapartum fetal monitoring, comprising:
   a base assembly having a bottom and containing a photodetector situated on said bottom of the base assembly;
   a collar surrounding the bottom of the base assembly;
   a single spiral probe extending through the photodetector and from the base assembly, and being surrounded by said collar, which probe is adapted to penetrate a fetal scalp;
   said probe containing an optical fiber having an end which functions as a light source which directs an emerging cone of light surrounded by said collar and toward said photodetector, said spiral probe having a closed end and a side opening directed towards said photodetector, and said light source being located in said side opening in said spiral probe;
   means for connecting said photodetector to an external monitor; and
   means for connecting said spiral probe to said external monitor;
   whereby said internal apparatus measures the arterial hemoglobin oxygen saturation and the fetal heart rate and EKG activity of the fetus.

2. The internal apparatus as claimed in claim 1, further comprising a flexible hollow guide tube having an inner diameter and a proximal end and a distal end; and
   said guide tube containing therewithin said base assembly at the proximal end.

3. The internal apparatus as claimed in claim 2, wherein said guide tube contains therewithin said spiral probe at the proximal end.

4. The internal apparatus as claimed in claim 2, further comprising a flexible hollow inner tube having a distal end an outer diameter smaller than the inner diameter of the guide tube;
   said inner tube being connected to the base assembly and located within said guide tube.

5. The internal apparatus as claimed in claim 4, further comprising a handle means adjacent to the distal end of said inner tube for rotating said inner tube.

6. The internal apparatus as claimed in claim 4, wherein said flexible hollow inner tube contains said means for connecting said photodetector to said external monitor.

7. The internal apparatus as claimed in claim 4, wherein said flexible hollow inner tube contains said means for connecting said spiral probe to said external monitor.

8. The internal apparatus as claimed in claim 5, further comprising:
   said optical fiber extending from the handle means at the distal end through said inner tube to said base assembly; and
   said connecting means for connecting said photodetector and said probe to said external monitor are wrapped around said optical fiber.

9. An internal apparatus for continuous electrical and oximetric intrapartum fetal monitoring comprising:
   a cylindrical base element having a proximal end surface and a distal end surface;
   a photodetector element situated at the said distal end surface of the said cylindrical base element wherein the said photodetector element occupies nearly the entire said distal end surface of the said cylindrical base element and does not penetrate a fetal skin surface;
   a spiral probe comprising a single spiral shaped needle configuration, having a proximal portion and an end portion, where the spiral probe needle originates in the said base element, traverses the photodetector element, and extends distally of the said base element distal end surface;
   the said probe containing an optical fiber said probe having a side opening in the said spiral probe needle;
   the said spiral needle having an end portion beveled to penetrate a fetal skin surface;
   the said probe containing said optical fiber having an end which functions as a light source which directs light from the said side opening in the said spiral probe toward the said photodetector, the said spiral probe having said side opening directed towards the said photodetector when said probe is inserted beneath a skin surface;
   means for connecting the said optical fiber to an external light source;
   means for connecting the said power control means to an external power supply;
   means for connecting the said spiral probe to an external monitor;
   means for connecting the said photodetector to said external monitor; and
   whereby said internal apparatus measures the arterial hemoglobin oxygen saturation and the fetal heart rate and EKG activity of the fetus during the labor and delivery process.

10. The internal apparatus as claimed in claim 9, wherein said photodetector is encircled by a rubber collar to provide protection from ambient light and surface impediments.

11. The internal apparatus as claimed in claim 9, wherein said spiral probe is electrically conductive to allow for fetal heart rate and EKG monitoring.

12. The internal apparatus as claimed in claim 9, wherein said optical fiber is contained entirely within the spiral needle and does not extend beyond it.

13. The internal apparatus as claimed in claim 9, wherein the said external light source is connected to power control means for regulating the amount of light transmitted by external said light source.

14. The internal apparatus as claimed in claim 9, wherein a cylindrical metal housing is contained within the said base element having a longitudinal central axis containing the said connecting means of the said spiral probe and the said photodetector to said external monitor.

15. The internal apparatus as claimed in claim 14, wherein the said optical fiber is stabilized and positioned by the said cylindrical metal housing to facilitate entry of the said optical fiber into the said spiral needle.

16. The internal apparatus as claimed in claim 9, further comprising means for insertion of the spiral probe into the fetal scalp.

* * * * *